(12) United States Patent
Adahan

(10) Patent No.: US 8,506,554 B2
(45) Date of Patent: Aug. 13, 2013

(54) WOUND CLOSURE AND DRAINAGE SYSTEM

(76) Inventor: Carmeli Adahan, Jerusalem (IL)

( * ) Notice: Subject to any disclaimer, the term of this patent is extended or adjusted under 35 U.S.C. 154(b) by 585 days.

(21) Appl. No.: 11/989,297

(22) PCT Filed: Jul. 24, 2005

(86) PCT No.: PCT/IL2005/000784
§ 371 (c)(1),
(2), (4) Date: Jan. 24, 2008

(87) PCT Pub. No.: WO2007/013049
PCT Pub. Date: Feb. 1, 2007

(65) Prior Publication Data
US 2009/0264837 A1  Oct. 22, 2009

(51) Int. Cl.
*A61M 1/00* (2006.01)
(52) U.S. Cl.
USPC ............ 604/540; 604/35; 604/305; 604/306; 604/307; 604/308; 604/313; 604/317; 604/318; 604/319; 604/320; 604/321; 604/322; 604/323; 604/541; 604/542; 604/543; 604/544; 604/902; 606/131
(58) Field of Classification Search
USPC ................................ 604/540–544
See application file for complete search history.

(56) References Cited

U.S. PATENT DOCUMENTS

| | | |
|---|---|---|
| 599,333 A | 2/1898 | Hulse |
| 1,599,899 A | 9/1926 | Kettering et al. |
| 3,416,461 A | 12/1968 | McFarland |
| 3,516,160 A * | 6/1970 | Leffler ............................. 433/95 |
| 4,108,574 A | 8/1978 | Bartley et al. |
| 4,208,171 A | 6/1980 | Jonsson |
| 4,447,226 A | 5/1984 | Mayoral |
| 4,552,552 A | 11/1985 | Polaschegg et al. |
| 4,583,970 A | 4/1986 | Kirchner |
| 4,611,627 A | 9/1986 | Eidsvoog et al. |
| 4,661,093 A | 4/1987 | Beck et al. |

(Continued)

FOREIGN PATENT DOCUMENTS

| | | |
|---|---|---|
| DE | 24 01 643 A1 | 7/1975 |
| DE | 32 05 445 A1 | 8/1983 |

(Continued)

OTHER PUBLICATIONS

Worth et al., "Preliminary Report The Effectiveness of Bacterial Filtration In Vented Wound Drains" Journal of Surgical Research 27(6):405-407 (1979).

(Continued)

*Primary Examiner* — Michele M. Kidwell
*Assistant Examiner* — Ilya Treyger
(74) *Attorney, Agent, or Firm* — Browdy and Neimark, PLLC

(57) ABSTRACT

The invention relates to a tilt and slide cover in a vehicle roof. The tilt and slide cover comprises a cover and a frame, which is supported in lateral guides of a roof opening. The special feature of the tilt and slide cover lies in the fact that the cover is arranged relatively moveable in relation to the frame and can be locked to and released from this. The frame comprises a plastic section, into which the slide guide and other fittings such as slide cheek holders or the like can be integrated in one piece. It is also possible to fix the rear water collection channel directly on the frame.

29 Claims, 2 Drawing Sheets

(56) References Cited

U.S. PATENT DOCUMENTS

| | | |
|---|---|---|
| 4,739,791 A | 4/1988 | Adahan |
| 4,930,997 A | 6/1990 | Bennett |
| 5,116,206 A | 5/1992 | Adahan |
| 5,370,610 A | 12/1994 | Reynolds |
| 5,419,687 A | 5/1995 | Adahan |
| 5,578,006 A | 11/1996 | Stevens |
| 5,636,643 A | 6/1997 | Argenta et al. |
| 5,645,081 A | 7/1997 | Argenta et al. |
| 5,662,599 A | 9/1997 | Reich et al. |
| 5,776,119 A | 7/1998 | Bilbo et al. |
| 5,941,859 A * | 8/1999 | Lerman .................. 604/289 |
| 5,947,923 A | 9/1999 | Uehara et al. |
| 6,042,560 A | 3/2000 | Niederberger |
| 6,071,267 A | 6/2000 | Zamicrowski |
| 6,257,847 B1 | 7/2001 | Silver et al. |
| 6,471,982 B1 | 10/2002 | Lydon et al. |
| 6,562,013 B1 | 5/2003 | Marasco, Jr. |
| 6,648,862 B2 | 11/2003 | Watson |
| 6,817,996 B2 | 11/2004 | Fard et al. |
| 6,824,533 B2 | 11/2004 | Risk, Jr. et al. |
| 7,128,735 B2 | 10/2006 | Weston |
| 7,229,422 B2 | 6/2007 | Klobe |
| 7,255,681 B1 | 8/2007 | Silver et al. |
| 7,503,910 B2 | 3/2009 | Adahan |
| 2001/0029956 A1 | 10/2001 | Argenta et al. |
| 2002/0151826 A1 | 10/2002 | Ramey et al. |
| 2003/0014022 A1 | 1/2003 | Lockwood et al. |
| 2003/0040687 A1 | 2/2003 | Boynton et al. |
| 2003/0050594 A1 | 3/2003 | Zamicrowski |
| 2003/0097100 A1 | 5/2003 | Watson |
| 2004/0015042 A1 | 1/2004 | Vincent et al. |
| 2004/0039243 A1 | 2/2004 | Bearnson et al. |
| 2004/0059284 A1 | 3/2004 | Nash et al. |
| 2004/0064132 A1 | 4/2004 | Bochringer et al. |
| 2004/0199840 A1 | 10/2004 | Takeoka et al. |
| 2005/0004534 A1 | 1/2005 | Lockwood et al. |
| 2005/0148913 A1 | 7/2005 | Weston |
| 2005/0180868 A1 | 8/2005 | Miller |
| 2005/0192548 A1 | 9/2005 | Dolliver et al. |

FOREIGN PATENT DOCUMENTS

| | | |
|---|---|---|
| DE | 32 05 449 C2 | 9/1983 |
| DE | 102 15 896 A1 | 10/2003 |
| EP | 0 156 211 A2 | 10/1985 |
| EP | 0865304 B1 | 7/2001 |
| GB | 2 307 180 A | 5/1997 |
| GB | 2 378 734 A | 2/2003 |
| JP | 2002035111 A | 2/2002 |
| JP | 2002541978 A | 12/2002 |
| RU | 240188 | 11/1947 |
| WO | 8401904 A1 | 5/1984 |
| WO | 96/05873 A1 | 2/1996 |
| WO | 97/18007 A1 | 5/1997 |
| WO | 9748427 A2 | 12/1997 |
| WO | 00/02016 A1 | 1/2000 |
| WO | 00/21586 A1 | 4/2000 |
| WO | 0064394 A1 | 11/2000 |
| WO | 01/34223 A1 | 5/2001 |
| WO | 03/016719 A1 | 2/2003 |
| WO | 03/030966 A1 | 4/2003 |
| WO | 03/057070 A2 | 7/2003 |
| WO | 2005/061025 A1 | 7/2005 |
| WO | WO 2008/039314 A2 * | 9/2006 |
| WO | WO 2008/039223 A1 * | 1/2007 |

OTHER PUBLICATIONS

Levite et al., "Possibilities for Dual-Lumen Drainages in Surgery" Body of the RSFSR Ministry of Public Health, Monthly Scientific and Practical Journal, pp. 39-41. (1987).

Notice of opposition to European patent EP2127690, dated Mar. 20, 2013.

Facts and Submissions in Opposition of EP 2127690, dated Mar. 20, 2013.

Edlich et al., "Evaluation of a New, Improved Surgical Drainage System" New Instruments, 149:295-298 (Feb. 1985).

Communication of a notice of opposition of EP 2127690, dated Apr. 8, 2013.

* cited by examiner

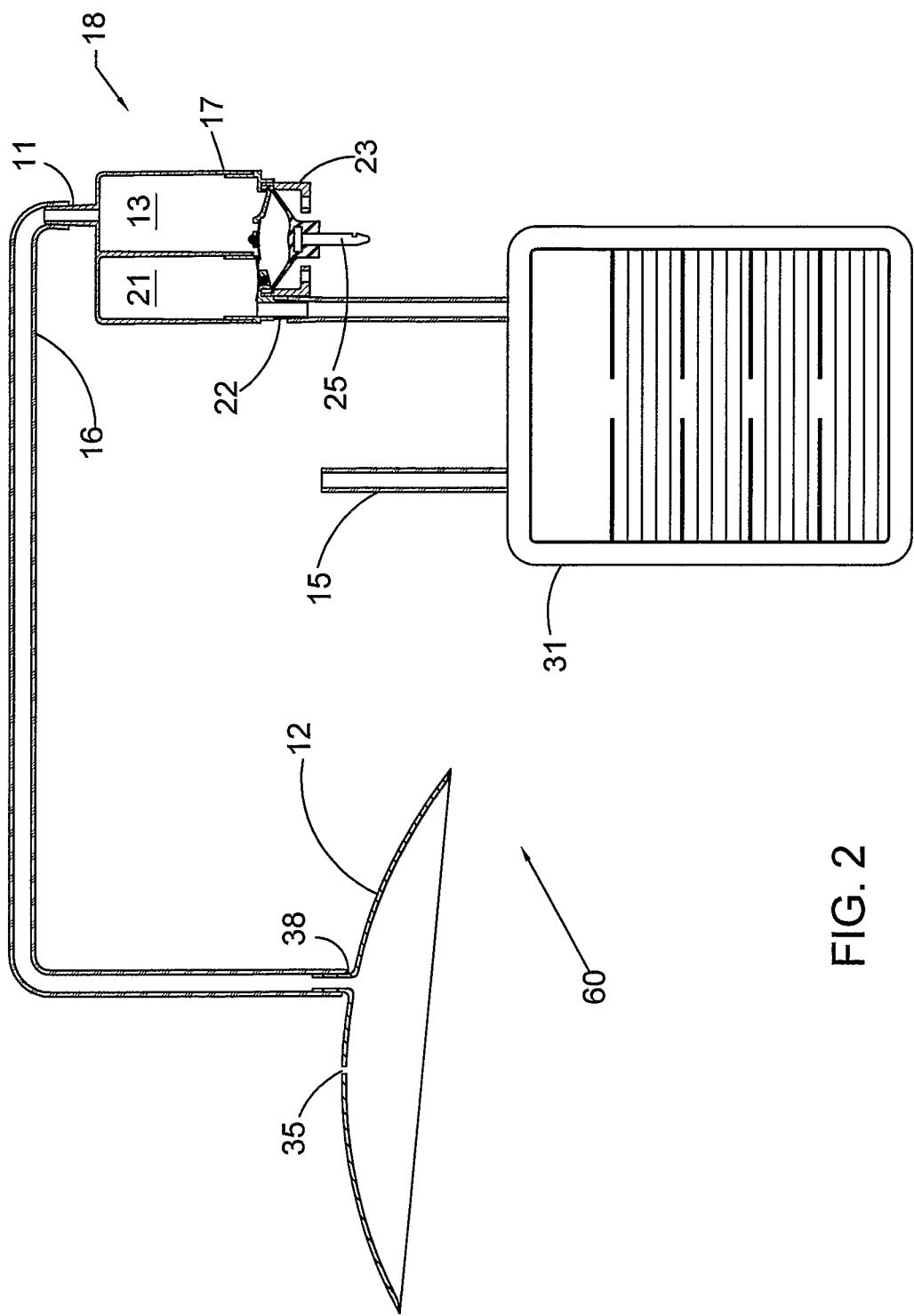

WOUND CLOSURE AND DRAINAGE SYSTEM

FIELD OF TH INVENTION

This invention relates generally to wound healing, and more specifically to healing of wounds by negative pressure drainage.

BACKGROUND OF THE INVENTION

Negative pressure applied to a wound enhances drainage of fluids or exudate from the wound and promotes tissue growth and wound healing. This method of healing (known as "cupping") was exercised since the times of ancient Greek physicians until the 19th century.

WO 96/05873 describes a therapeutic apparatus for stimulating healing of wounds. The apparatus comprises a porous foamed pad which is sealed on the wound and connected by a tube to an inlet of a canister. A vacuum pump is connected to an outlet of the canister. A bacterial filter positioned over the outlet of the canister protects the vacuum pump from contamination by wound drainage fluids sucked into the canister. The pump, the canister and control circuitry are disposed in a case.

WO 97/18007 discloses a portable wound treatment apparatus using a similar arrangement of a porous pad, canister and vacuum pump. The canister and the pump are in one housing which accommodates also the control circuitry and is wearable on a harness or a belt.

U.S. Pat. No. 6,648,862 describes a portable vacuum desiccator using a similar arrangement as above, the canister being formed as a cartridge containing a trapping agent (desiccator). The vacuum pump and the canister may be integrated and detachable from the pump motor and circuitry.

Current negative pressure wound drainage systems such as the ones described above suffer from the following deficiencies:

Since the negative pressure applied to the wound area is created by pump suction, the flow into the pump is likely to contaminate the pump, or conversely, to require costly and complex methods of isolating the pump from the wound exudate such as antibacterial filters.

The wound exudate is collected in a rigid canister, which must be large enough to prevent it from overflowing, and thus it is bulky and an inconvenient burden for ambulatory patients, who carry a portable system with them.

Conventional wound drainage systems utilize an air tight seal of the wound, which is helpful in obtaining and maintaining negative pressure, but requires a pressure relief or bleed valve to produce the pressure cycling desirable to obtain accelerated wound closure, as described in WO 96/05873.

A sealed wound dressing or enclosure, when under negative pressure, will promote migration of the exudate toward the negative pressure source, through the connecting tube, which may occlude, should the exudate coagulate.

The need to monitor and control the negative pressure level in conventional systems requires the use of a vacuum transducer, gage or relief valve, which must be connected to the suction tube, which is subject to contamination. Cleaning, disinfecting or isolating the negative pressure monitoring or controlling device are complex, costly and un-reliable.

SUMMARY OF THE INVENTION

It is the purpose of this invention to alleviate all the above listed deficiencies, by providing a wound drainage enclosure and vacuum system, which are impervious to contamination and easy to use.

In accordance with a first aspect of the present invention, there is provided an enclosure for draining an open wound from liquids exuded therefrom. The enclosure is attachable to the wound circumference so as to define a confined volume, and has an outlet, for example formed as a nipple, connectable by means of a tube to an inlet of a vacuum pump so that negative pressure may be created in said confined volume. One or more bleeding holes are provided in the enclosure or adjacent to its outlet such that ambient air can enter the tube and flow together with the exuded liquids when negative pressure is present. Ambient pressure may be restored in the confined volume when the vacuum pump is not operating.

The bleeding hole in the enclosure may be a calibrated orifice or other flow restrictors providing for controlled flow of ambient air into the enclosure or into its outlet. For instance, a hole plugged with open cell foam or an open pore sintered metal plug, which restrict the flow, but are not susceptible to plugging as is a small orifice.

The bleeding hole renders the wound closure vented or non-airtight, as distinguishable from conventional wound closures. The flow of air from the bleeding hole in the wound closure, in response to the negative pressure created by the vacuum pump, facilitates the removal of exudate, which might otherwise coagulate, dry-up and occlude the tubing.

According to another aspect of the present invention, there is provided a method for draining an open wound from liquids exuded therefrom. The method includes:

providing an enclosure and sealing it to the wound circumference so as to define a confined volume,
connecting the confined volume to a vacuum pump,
connecting a waste container for collection of drained liquids to the vacuum pump, and
operating said vacuum pump to draw the exuded liquids from the wound.

The method is characterized in that the confined volume is connected to an inlet of the vacuum pump and the waste container is connected to an outlet of the vacuum pump such that the drained liquids flow through said vacuum pump.

The method may include employment of an enclosure with bleeding orifices so that ambient air is allowed to enter the tube and flow together with the drained exuded liquids.

Preferably, gases are separated and released from the drained exuded liquids.

According to a further aspect of the present invention, there is provided a vacuum system for practicing the above method. The vacuum system may use a totally disposable vacuum pump, together with a waste collection bag, as disclosed in WO03016719. The vacuum pump is a two-chambered diaphragm pump adapted for pumping gases and liquids and/or any combination thereof The vacuum pump is capable of pumping air and fluid which enter its inlet port, to a waste bag attached to its outlet port. The waste bag is vented to the atmosphere, such that it collects only the fluids which enter it.

The vacuum system may be adapted to be carried by an ambulatory patient.

According with a next aspect of the present invention, there is provided a disposable assembly for draining an open wound from liquids exuded therefrom. The assembly comprises an enclosure attachable to the wound circumference so as to define a confined volume, a vacuum pump unit connected to the enclosure so that negative pressure may be created in the confined volume, and a waste container connected to the vacuum pump unit. The vacuum pump unit has means for detachably attaching to a drive unit for operating the pump unit. The enclosure is connected to an inlet of the vacuum pump unit and the waste container is connected to an outlet of the vacuum pump unit, such that when the vacuum pump unit is operated the drained liquids flow therethrough.

Preferably, the pump unit and the drive unit are adapted for attaching and detaching by simple hand manipulations.

The enclosure may have bleeding holes as described above.

The vacuum pump unit is preferably a two-chambered diaphragm pump adapted for pumping gases and liquids and/or any combination thereof.

The waste container may contain a porous media adapted to soak up the drained liquids and may be in the form of a collapsible or foldable bag.

The drained liquids and air contact only the parts of the disposable assembly. The drained exuded liquids may then be disposed of together with the disposable assembly. More specifically, the pump unit is disposed of after use, together with the tubing connected to it, as well as the waste bag connected, with its content, and with the wound closure which may be connected to the pump unit via the tube.

In accordance with yet another aspect of the present invention, there is provided a vacuum system as described above where the vacuum pump has a drive unit and a control block adapted to power the drive unit so that a predetermined level of negative pressure is maintained in the confined volume. The control block has a sensor for sensing working parameters of the drive unit and means for deriving the level of negative pressure in the confined volume from these working parameters, in order to maintain said predetermined level. The sensor has no fluid connection with the confined volume.

For example, the drive unit may comprise a direct current electric motor and the sensor may sense the electric current driving the motor. The same function of negative pressure control may be accomplished by an adjustable torque limiting clutch, placed between the motor output shaft and the pump.

The control block may be provided with alarm means to warn the user if the predetermined level of negative pressure is not maintained.

If the vacuum pump comprises a disposable pump unit and the drive unit is detachably attachable to the pump unit, the control block with monitoring means is preferably associated with the drive unit which is non-disposable.

Thus, indirect means are provided for controlling or monitoring the level of negative pressure applied to the wound, without making any direct connection to a vacuum sensor, transducer or gage to any portion of the system, which has the negative pressure applied to it. The indirect negative pressure monitoring and control result from the need to dispose of any portion of the system, which may come in contact with the pumped media, which is likely to be contaminated or infectious. Accordingly, all the disposable components in the system may be relatively low in cost, to promote discarding them after use. Pressure transducers, vacuum gages or sensors, are relatively costly, and thus not considered disposable.

BRIEF DESCRIPTION OF THE DRAWINGS

In order to understand the invention and to see how it may be applied, a preferred embodiment will now be described, by way of non-limiting example only, with reference to the accompanying drawings, in which:

FIG. 2 shows the disposable portion of the system of FIG. 1.

DETAILED DESCRIPTION OF EXEMPLARY EMBODIMENTS

Figure 1:
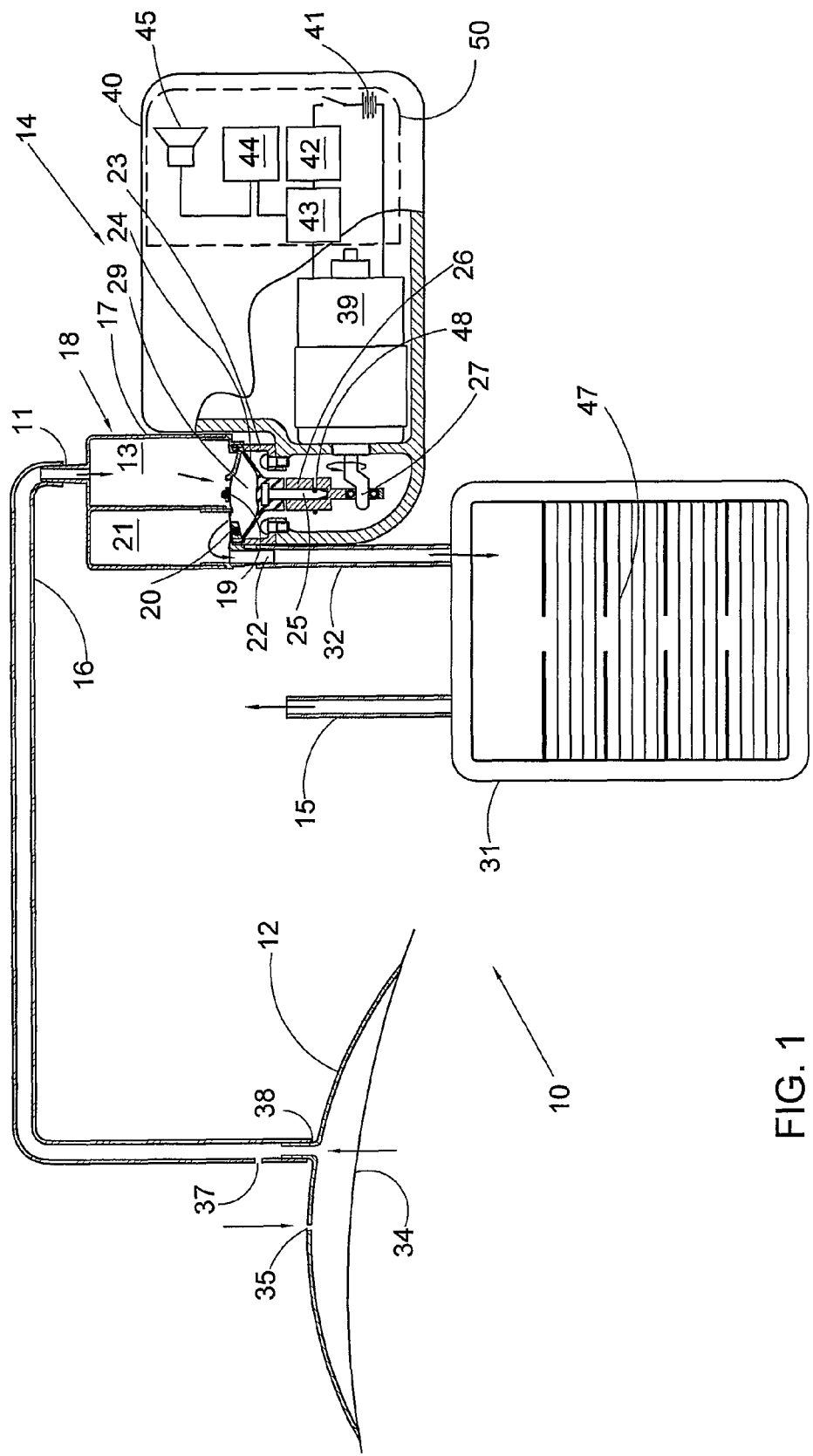
FIG. 1 is a schematic sectional view of the vacuum system of the present invention applied on a wound.

The present invention provides a system and a method of treating and healing of a body wound, by applying a negative pressure to the wound, over an area sufficient to promote migration of epithelial and subcutaneous tissue toward the wound.

It is appreciated that the detailed description that follows is intended only to illustrate certain preferred embodiments of the present invention. It is in no way intended to limit the scope of the invention, as set out in the claims.

With reference to FIG. 1, in accordance with the present invention, a vacuum system 10 for draining an open wound from liquids exuded therefrom comprises a wound enclosure 12, a vacuum pump 14, and waste collection bag 31. The wound enclosure 12 is connected by a suction tube 16 to an inlet 11 of the vacuum pump. The waste collection bag 31 is connected to an outlet 22 of the vacuum pump. Thereby, when the vacuum pump 14 is operated, the drained liquids flow through the pump into the waste bag 31.

Suction tube 16 is connected to nipple 38 of the enclosure 12 which covers wound area of the body 34 such that suction of air through tube 16 creates negative pressure in the volume above the wound area of the body 34. A bleeding orifice 35 is provided within the enclosure 12, or adjacent to it as a tube orifice 37 (i.e. venting arrangement), allowing ambient air to flow into and through suction tube 16, rendering enclosure 12 non-air tight, or vented. This feature, unlike conventional sealed closures, provides for quick movement of exudate entering suction tube 16, toward the vacuum pump 14, and into the waste bag 31, before it dries up or coagulates and occludes the tube. This feature also provides for introduction of ambient pressure to the wound area of the body 34 whenever the vacuum pump stops pumping, allowing cyclic negative pressure application to the wound, by cycling the vacuum pump on and off alternately.

Instead of the bleeding orifice 35 in the enclosure, other flow restrictors may be used to provide for controlled flow of ambient air into the enclosure or into the outlet. For instance, a hole plugged with open cell foam or an open pore sintered metal plug, which restrict the flow, but are not susceptible to plugging as is a small orifice.

The vacuum pump 14 comprises a pump unit 18 and a drive unit 40 which are detachably attachable to each other, as explained below. The pump unit 18 includes a two-chambered housing 17 and a diaphragm 24 secured to the underside of the two-chambered housing 17 so as to form a working chamber 29.

The two-chambered housing 17 has a first chamber 13 with the inlet 11 and a second chamber 21 with an outlet 22. The suction tube 16 is connected to the inlet 11. Two one-way valves 19 and 20 are present at the bottom of the first chamber 13 and the second chamber 21, respectively. To the bottom of the two-chambered housing 17 there is attached a mounting base 23, used to mount the housing 17 to the drive unit 40 by means of a bayonet lock.

The diaphragm 24 has an integral rod-shaped drive member 25, which is used for engagement with the drive unit 40.

The drive unit 40 includes an electric motor 39, batteries 41 and a control block 50 described below. The shaft of the motor 39 has a crank 27 coupled to a reciprocating rod 26. The rod 26 has a receptacle with a cavity adapted to receive and lock therein the drive member 25.

When the pump unit 18 is attached to the drive unit 40 by means of the bayonet lock in the base 23, the drive member 25 is received in the receptacle cavity of the reciprocating rod 26 and then locked therein.

Upon activation of the motor 39, the crank 27 is rotated and reciprocates the receptacle rod 26, causing the diaphragm 24 to expand and contract the working chamber 29. Thus the pump unit 18 pumps air or liquid that passes through the one-way valves 19 and 20.

Air and liquids enter the two-chambered housing 17 through the inlet 11 and suction tube 16 which is connected to the patient's wound enclosure 12, for the removal of exudate. Liquids and air enter the first chamber 13, which is under negative pressure when diaphragm 24 reciprocates, driving them past one-way valve 20, into the second chamber 21. The air and liquid which are pumped through outlet 22, enter waste bag 31.

The pump's ability to pump air and liquid, unlike conventional pumps, which are efficient in pumping only one type of matter, is enhanced by the flexibility of the diaphragm 24 which allows the diaphragm to yield when encountering heavy loads, such as those present when pumping liquid. This diaphragm flexibility also provides an additional substantial advantage: when the negative pressure in working chamber 29 is high, the diaphragm 24 stretches to allow the reciprocation of the receptacle rod 26 to occur, at minimal burden to the electric motor 39.

The waste bag 31 has a vent 15, through which air and gas are discharged to the atmosphere. Accordingly, waste bag 31 will retain only the waste fluids which are pumped into it. The waste bag may contain a porous media 47 adapted to soak up the drained liquids.

It is important to note that waste bag 31 is made of thin plastic sheet, which allow it to be folded or collapsed when not full, providing the convenience of having minimal bulk and minimal inconvenience to the patient using or carrying it.

The drive unit 40 also includes a control block 50 with control circuits such as cycle control 42, which turns the motor pump on and off alternately, motor voltage and current monitoring and control 43, which controls the negative pressure level produced by the pump unit 18, by controlling the voltage and current which drive motor 39. At any given voltage which drives motor 39, the current draw of the motor is directly related to the negative pressure generated by the pump 18. Accordingly, monitoring of the current which the motor 39 draws allows for indirect monitoring of the negative pressure attained by pump 18. The ability to monitor the negative pressure developed by pump 18, indirectly, precludes the need of making an infectious negative pressure line connection to a pressure transducer or vacuum gage.

For example, if the motor 39 is a direct current electric motor, a sensor may sense the electric current driving the motor. Since the direct current motor output torque is directly related to the current driving the motor, and since the motor output torque is directly related to the negative pressure the pump 18 produces, monitoring the motor current or controlling it, provide for monitoring and controlling the negative pressure produced by the vacuum pump. Motor current monitoring is only one of the available methods of indirect negative pressure monitoring and controlling. The same function of negative pressure control may be accomplished by an adjustable torque limiting clutch placed between the motor output shaft and the crank 27.

The control block 50 also has a negative pressure comparator 44, which compares the desired set negative pressure level obtained by pump 18, and the actual monitored negative pressure level as obtained indirectly from motor voltage and current monitoring and control 43. Comparator 44 will activate audible alarm 45, whenever pump 18 fails to reach the desired pre-set negative pressure level.

FIG. 2 shows the disposable portion of the system as an assembly 60, which includes the pump unit 18, the waste bag 31, the connecting tube 16 and the wound enclosure 12, all separated from the drive unit and from the wound area of the body 34. The assembly 60 may be disposed of in its totality after use, and replaced by a new assembly, thus keeping the costly drive unit 40 free from any contamination. It would be obvious to those skilled in the art, that the present invention alleviates the need for cleaning or disinfecting any portion of drive unit 40 after use, or providing protective means, such as filters, to keep contaminants from reaching the costly drive 40.

The invention claimed is:

1. An enclosure for applying negative pressure to a wound, the enclosure being attachable to the wound circumference so as to define a confined volume, and comprising a tube and a venting arrangement, the enclosure having an enclosure outlet connectable to a vacuum source via said tube so that negative pressure can be selectively created in said volume, said venting arrangement located outside said enclosure and comprising a flow restrictor to restrict flow through said venting arrangement located outside said enclosure and comprising a flow restrictor such that ambient air can enter said tube via said venting arrangement and flow to said vacuum source without having to enter said enclosure.

2. The enclosure according to claim 1, wherein said venting arrangement comprises one or more bleeding holes.

3. The enclosure according to claim of claim 1, wherein said venting arrangement is provided in the form of a porous body.

4. The enclosure according to claim 1, wherein said venting arrangement acts to provide, under the action of the vacuum source, a restricted flow of ambient air therethrough and along said tube.

5. The enclosure according to claim 1, wherein said enclosure facilitates drainage of fluids exuded from the wound, wherein the ambient air can enter said tube via said venting arrangement and flow together with the exuded liquids under the action of the negative pressure.

6. The enclosure according to claim 1, wherein said venting arrangement provides for ambient air to enter said enclosure via said tube and for ambient pressure to be restored in said confined volume when the vacuum source is not operating.

7. The enclosure according to claim 1, wherein in operation of the enclosure, ambient air enters the tube directly via said venting arrangement without entering said enclosure when negative pressure is being applied to the wound via said enclosure.

8. A disposable assembly for applying negative pressure to a wound, the assembly comprising an enclosure as defined in claim 1 attachable to the wound circumference so as to define a confined volume, a vacuum pump unit of the vacuum pump connected to said enclosure so that negative pressure may be created in said volume, said vacuum pump unit being configured for being detachably attached to a drive unit of the vacuum pump for operating the pump unit, and a waste container connected to said vacuum pump unit, wherein said enclosure is connected to an inlet of said vacuum pump unit via said tube and said waste container is connected to an outlet of said vacuum pump unit.

9. A disposable assembly according to claim 8, wherein said assembly further operates to drain the wound from fluids exuded therefrom, wherein the ambient air can enter said tube via said venting arrangement and flow together with the exuded liquids under the action of the negative pressure, and facilitates draining of the exuded fluids to said waste container.

10. The disposable assembly according to claim 8, wherein said venting arrangement comprises one or more bleeding holes.

11. The disposable assembly according to claim 8, wherein said venting arrangement is provided in the form of a porous body.

12. A vacuum system for applying negative pressure to a wound, the vacuum system comprising; an enclosure and a vacuum source, the enclosure being attachable to the wound circumference so as to define a confined volume;
  a tube;
  a venting arrangement comprising a flow restrictor to restrict flow through said venting arrangement, the enclosure having an enclosure outlet connectable to said vacuum source via said tube so that negative pressure can be created in said volume, said venting arrangement located outside said enclosure such that ambient air can enter said tube via said venting arrangement without entering said enclosure; and
  a waste container in fluid communication with said vacuum source.

13. The vacuum system of claim 12, wherein said vacuum system further operates to drain the wound from fluids exuded therefrom, wherein the ambient air can enter said tube via said venting arrangement and flow together with the exuded liquids under the action of the negative pressure, and facilitates draining of the exuded fluids to said waste container.

14. The vacuum system according to claim 12, wherein said vacuum source includes a disposable pump unit detachably attachable to a non-disposable drive unit, said enclosure and said waste container being disposable so that the ambient air that enters said tube via said venting arrangement contacts only the disposable elements and said drained liquids may be disposed of together with said disposable elements.

15. The vacuum system according to claim 14, wherein said pump unit and said drive unit are adapted for attaching and detaching by simple hand manipulations.

16. The vacuum system according to claim 12, wherein said venting arrangement comprises one or more bleeding holes.

17. The vacuum system according to claim 12, wherein said venting arrangement is provided in the form of a porous body.

18. A vacuum system for applying a negative pressure to a wound, the vacuum system comprising an enclosure and a vacuum source, the enclosure being attachable to the wound circumference so as to define a confined volume, and comprising a tube, the enclosure having an enclosure outlet connectable to said vacuum source via said tube so that negative pressure may be created in said volume, said tube comprising a venting arrangement comprising a flow restrictor to restrict flow through said venting arrangement located adjacent to said enclosure outlet and outside said enclosure such that ambient air can enter said tube via said venting arrangement and flow to said vacuum source without entering said enclosure, wherein said vacuum pump comprises a collection chamber upstream of a pump inlet of said vacuum source, and wherein said tube is connected to an inlet of said collection chamber.

19. The vacuum system of claim 18, wherein said vacuum system further operates to drain the wound from fluids exuded therefrom, wherein the ambient air can enter said tube via said venting arrangement and flow together with the exuded liquids under the action of the negative pressure, and facilitates draining of the exuded fluids to said waste container.

20. The vacuum system according to claim 18, wherein said vacuum source includes a disposable pump unit detachably attachable to a non-disposable drive unit, said enclosure and said collection chamber being disposable so that the ambient air that enters said tube via said venting arrangement contacts only the disposable elements and said drained liquids may be disposed of together with said disposable elements.

21. The vacuum system according to claim 20, wherein said pump unit and said drive unit are adapted for attaching and detaching by simple hand manipulations.

22. The vacuum system according to claim 18, wherein said venting arrangement comprises one or more bleeding holes.

23. The vacuum system according to claim 18, wherein said venting arrangement is provided in the form of a porous body.

24. The vacuum system according to claim 1, wherein the venting arrangement is a tube orifice.

25. The enclosure according to claim 24, said orifice having a smaller opening than a cross-section of the tube.

26. The vacuum system according to claim 12, wherein the venting arrangement is a tube orifice.

27. The enclosure according to claim 26, said orifice having a smaller opening than a cross-section of the tube.

28. The vacuum system according to claim 18, wherein the venting arrangement is a tube orifice.

29. The enclosure according to claim 28, said orifice having a smaller opening than a cross-section of the tube.

* * * * *

UNITED STATES PATENT AND TRADEMARK OFFICE
CERTIFICATE OF CORRECTION

PATENT NO. : 8,506,554 B2  
APPLICATION NO. : 11/989297  
DATED : August 13, 2013  
INVENTOR(S) : Carmeli Adahan Page 1 of 1

It is certified that error appears in the above-identified patent and that said Letters Patent is hereby corrected as shown below:

Title Page, Item (57) Abstract should read:
A vacuum system for draining an open wound from liquids exuded therefrom, comprising an enclosure sealable to the wound circumference, a vacuum pump including a disposable pump unit detachably attachable to a non-disposable drive unit, and a waste container for collection of drained liquids. The enclosure has an outlet connected by means of a tube to an inlet of the pump unit and the waste container is connected to an outlet of the pump unit, such that when the vacuum pump is operated the drained liquids flow through the vacuum pump. The enclosure has one or more bleeding holes provided therethrough or adjacent to its outlet so that ambient air may enter the tube and flow together with the drained liquids. The enclosure and the waste container are disposable so that the drained liquids contact only disposable elements and may be disposed of together with all disposable elements.

Signed and Sealed this  
Fifteenth Day of April, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,506,554 B2
APPLICATION NO. : 11/989297
DATED : August 13, 2013
INVENTOR(S) : Carmeli Adahan Page 1 of 1

It is certified that error appears in the above-identified patent and that said Letters Patent is hereby corrected as shown below:

In the Claims

Column 6, lines 17-28, Claim 1 should read

1. An enclosure for applying negative pressure to a wound, the enclosure being attachable to the wound circumference so as to define a confined volume, and comprising a tube and a venting arrangement, the enclosure having an enclosure outlet connectable to a vacuum source via said tube so that negative pressure can be selectively created in said volume, said venting arrangement located outside said enclosure and comprising a flow restrictor to restrict flow through said venting arrangement located outside said enclosure and comprising a flow restrictor such that ambient air can enter said tube via said venting arrangement and flow to said vacuum source without having to enter said enclosure.

Signed and Sealed this
Third Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 8,506,554 B2
APPLICATION NO.    : 11/989297
DATED              : August 13, 2013
INVENTOR(S)        : Carmeli Adahan Page 1 of 1

It is certified that error appears in the above-identified patent and that said Letters Patent is hereby corrected as shown below:

In the Claims

Column 6, lines 17-28, Claim 1 should read

1. An enclosure for applying negative pressure to a wound, the enclosure being attachable to the wound circumference so as to define a confined volume, and comprising a tube and a venting arrangement, the enclosure having an enclosure outlet connectable to a vacuum source via said tube so that negative pressure can be selectively created in said volume, said venting arrangement located outside said enclosure and comprising a flow restrictor to restrict flow through said venting arrangement such that ambient air can enter said tube via said venting arrangement and flow to said vacuum source without having to enter said enclosure.;

Column 6, line 31, Claim 3, delete "of claim";

Column 7, lines 10-13, Claim 12, rewrite these lines to read:

12. A vacuum system for applying negative pressure to a wound, the vacuum system comprising:
        an enclosure and a vacuum source, the enclosure being attachable to the wound
            circumference so as to define a confined volume;

Column 8, line 37, Claim 24, delete "vacuum system" and insert --enclosure--;

Column 8, line 43, Claim 27, delete "enclosure" and insert --vacuum system--;

Column 8, line 47, Claim 29, delete "enclosure" and insert --vacuum system--.

This certificate supersedes the Certificate of Correction issued June 3, 2014.

Signed and Sealed this
Ninth Day of September, 2014

Michelle K. Lee
*Deputy Director of the United States Patent and Trademark Office*